United States Patent
Boyxen et al.

(10) Patent No.: US 6,333,040 B1
(45) Date of Patent: Dec. 25, 2001

(54) COSMETIC PREPARATIONS

(75) Inventors: Norbert Boyxen, Kempen; Ansgar Behler, Bottrop; Hermann Hensen, Haan; Werner Seipel, Hilden, all of (DE)

(73) Assignee: Henkel Kommanditgesellschaft auf Aktien, Duesseldorf (DE)

( * ) Notice: Subject to any disclaimer, the term of this patent is extended or adjusted under 35 U.S.C. 154(b) by 0 days.

(21) Appl. No.: 09/381,406

(22) PCT Filed: Mar. 11, 1998

(86) PCT No.: PCT/EP98/01395

§ 371 Date: Dec. 6, 1999

§ 102(e) Date: Dec. 6, 1999

(87) PCT Pub. No.: WO98/41187

PCT Pub. Date: Sep. 24, 1998

(30) Foreign Application Priority Data

Mar. 19, 1997 (DE) .............................................. 197 11 417

(51) Int. Cl.⁷ .............................. A61K 7/00; A61K 7/02; A61K 7/035; A61K 7/48
(52) U.S. Cl. ..................... 424/401; 424/70.01; 554/90; 554/109
(58) Field of Search ................ 424/401, 70.01; 554/109, 90

(56) References Cited

U.S. PATENT DOCUMENTS

| 4,867,899 | * | 9/1989 | Ahmed et al. ................ 252/121 |
| 5,312,932 | * | 5/1994 | Behler et al. ..................... 554/90 |
| 5,322,957 | | 6/1994 | Fabry et al. ....................... 558/23 |
| 5,484,531 | | 1/1996 | Kuehne et al. ................... 210/653 |
| 5,489,395 | * | 2/1996 | Behler et al. ................. 252/174.17 |
| 5,494,938 | | 2/1996 | Kawa et al. ...................... 514/786 |
| 5,880,299 | * | 3/1999 | Ponsati Obiols et al. ........... 554/109 |
| 5,939,081 | * | 8/1999 | Ansmann et al. .................. 424/401 |

FOREIGN PATENT DOCUMENTS

| 11 65 574 | 3/1964 | (DE) . |
| 41 39 935 | 6/1993 | (DE) . |
| 42 04 700 | 8/1993 | (DE) . |
| 195 37 836 | 4/1997 | (DE) . |
| 195 43 633 | 5/1997 | (DE) . |
| 196 05 360 | 8/1997 | (DE) . |
| 196 35 553 | 3/1998 | (DE) . |
| 0 538 762 | 4/1993 | (EP) . |
| 0 561 825 | 9/1993 | (EP) . |
| 0 561 999 | 9/1993 | (EP) . |
| 22 52 840 | 12/1978 | (FR) . |
| 962 919 | 7/1964 | (GB) . |
| WO92/07543 | 5/1992 | (WO) . |

OTHER PUBLICATIONS

J.Am.Oil.Chem.Soc., vol. 37, pp. 171–175 (1960).
J.Am.Oil.Chem.Soc., vol. 67, pp. 8–14 (1990).
Surfactant in Consumer Products, pp. 61–63 (1987).
Kosmetische Faerbemittel, pp. 81–106 (1984).

* cited by examiner

*Primary Examiner*—Diana Dudash
*Assistant Examiner*—Mina Haghighatian
(74) *Attorney, Agent, or Firm*—John E. Drach; Henry E. Millson, Jr.

(57) ABSTRACT

Compositions having refatting properties for use in and as cosmetic preparations wherein the compositions contain
  (a) monoglyceride (ether) sulfates, and
  (b) fatty acid partial glycerides;
and processes for their preparation.

22 Claims, No Drawings

COSMETIC PREPARATIONS

This application is a 371 of PCT/EP98/01395, filed Mar. 11, 1998.

FIELD OF THE INVENTION

This invention relates to cosmetic preparations with refatting properties based on monoglyceride(ether)sulfates and fatty acid partial glycerides, to a process for their production by substoichiometric sulfation of partial glycerides and to the use of the mixtures for the production of cosmetic compositions with refatting properties.

BACKGROUND OF THE INVENTION

Preparations which are used to clean and care for the human skin and hair generally contain one or more surface-active substances, more especially based on anionic or amphoteric surfactants. Since the sole use of surfactants would excessively dry out the skin and hair, it is standard practice to add refatting agents to preparations of the type in question. It is obvious that these substances are expected to have not only an adequate refatting effect, but also—in line with market requirements—optimal dermatological compatibility.

German patent DE-C2 4139935 (Kao) describes liquid water-based body washes which contain 5 to 35% by weight of anionic surfactants, 2.5 to 15% by weight of alkyl polyglucosides and 0.5 to 15% by weight of saturated fatty acid monoglycerides containing 8 to 18 carbon atoms in the fatty acyl group. Unfortunately, the monoglycerides proposed in this document do not have adequate dermatological compatibility, even in admixture with glucosides. In addition, in the absence of water, the mixtures are generally solid and, for this reason, cannot be cold-processed. European patent EP-B1 0554292 (Henkel) describes o/w emulsions containing oils, alkyl polyglucosides, fatty acid partial glycerides and optionally fatty alcohols. These mixtures are also not entirely satisfactory in their refatting effect, their dermatological compatibility and their consistency in the absence of water. Finally, European patent application EP-A1 0538762 (Kao) describes hair treatment compositions containing cationic surfactants, alkyl polyglucosides and oils including, for example, fatty acid monoglycerides.

Accordingly, the complex problem addressed by the present invention was to provide refatting agents free from ethylene oxide which—at one and the same time—would be liquid at room temperature, would have thickening properties and, in particular, would show particularly high dermatological compatibility.

SUMMARY OF THE INVENTION

The present invention relates to cosmetic preparations with refatting properties containing (a) monoglyceride (ether)sulfates and (b) fatty acid partial glycerides.

It has surprisingly been found that the mixtures according to the invention combine particularly high dermatological compatibility with optimal refatting properties. In addition, the preparations are liquid at room temperature so that they may also be cold-processed. Another advantage is that the mixtures build up a viscosity in surfactant-containing systems.

DESCRIPTION OF THE PREFERRED EMBODIMENTS

Monoglyceride(ether)sulfates

Monoglyceride sulfates and monoglyceride ether sulfates are known anionic surfactants which may be obtained by the relevant methods of preparative organic chemistry. They are normally produced from triglycerides which—optionally after ethoxylation—are transesterified to the monoglycerides and then sulfated and neutralized. The partial glycerides may also be reacted with suitable sulfating agents, preferably gaseous sulfur trioxide or chlorosulfonic acid [cf. EP-B1 0561825, EP-B1 0561999 (Henkel)]. If desired, the neutralized products may be subjected to ultrafiltration In order to reduce their electrolyte content to a required level [DE-A1 4204700 (Henkel)]. Overviews on the chemistry of monoglyceride sulfates have been published, for example, by A. K. Biswas et al. in J. Am. Oil. Chem. Soc. 37, 171 (1960) and by F. U. Ahmed in J. Am. Oil. Chem. Soc. 67, 8 (1990). The monoglyceride (ether) sulfates suitable for use in accordance with the presence invention correspond to formula (I):

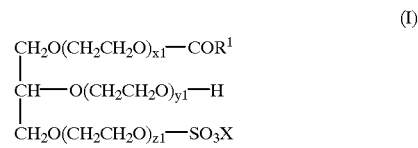

in which $R^1CO$ is a linear or branched acyl group containing 6 to 22 carbon atoms, x1, y1 and z1 together stand for 0 or for numbers of 1 to 30, preferably 2 to 10, and X is an alkali metal or alkaline earth metal. Typical examples of monoglyceride(ether)sulfates suitable for the purposes of the present invention are the reaction products of lauric acid monoglyceride, coconut oil fatty acid monoglyceride, palmitic acid monoglyceride, stearic acid monoglyceride, oleic acid monoglyceride and tallow fatty acid mono-glyceride and ethylene oxide adducts thereof with sulfur trioxide or chlorosulfonic acid in the form of their sodium salts. Monoglyceride sulfates corresponding to formula (I), in which $R^1CO$ is a linear acyl group containing 8 to 18 carbon atoms, are preferably used.

Fatty Acid Partial Glycerides

The fatty acid partial glycerides forming component (b) are known substances which may be prepared by the relevant methods of preparative organic chemistry and which correspond to formula (II):

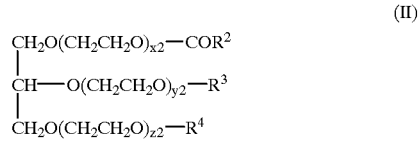

where $R^2CO$ is a linear or branched acyl group containing 6 to 22 carbon atoms, x2, y2 and z2 together stand for 0 or for numbers of 1 to 30, preferably 2 to 10, $R^3$ and $R^4$ independently of one another have the same meaning as $R^2CO$ or represent hydrogen, with the proviso that $R^3$ and $R^4$ cannot both be an acyl group. Fatty acid partial glycerides, i.e. generally technical mixtures of mono and diglycerides, are normally obtained by transesterifying the corresponding triglycerides with glycerol or by selective esterification of fatty acids. The removal of unreacted starting materials and the enrichment of monoglycerides in the mixtures are generally carried out by molecular distillation. The partial glycerides of the present invention are preferably obtained by esterification of glycerol with fatty acids containing 6 to 22 and preferably 12 to 18 carbon atoms, such as for example caproic acid, caprylic acid, 2-ethylhexanoic acid, capric acid, lauric acid, isotridecanoic acid, myristic acid, palmitic acid, palmitoleic acid, stearic acid, isostearic acid, oleic acid, elaidic acid, petroselic acid, linoleic acid, linolenic acid, elaeostearic acid, arachic acid, gadoleic acid, behenic acid and erucic acid and technical mixtures thereof. The present invention includes the observation that technical mono-/diglyceride mixtures have even better dermatological compatibility than the pure monoglycerides. Accordingly, technical fatty acid mono-/diglycerides which have a molar ratio of monoester to diester of 10:90 to 90:10 and, more particularly, 80:20 to 50:50 are preferred.

Mixtures of coconut oil monoglyceride sulfates and coconut oil fatty acid monoglycerides show particularly favorable performance properties and are therefore preferred. Components (a) and (b) are generally used in a ratio by weight of 30:70 to 99:1, preferably 50:50 to 90:10 and more preferably 70:30 to 80:20.

Alkyl and/or Alkenyl Oligoglycosides

In one preferred embodiment of the invention, the preparations contain as further surface-active ingredients alkyl and/or alkenyl polyglycosides corresponding to formula (III):

$$R^5O\text{---}[G]_p \tag{III}$$

in which $R^5$ is an alkyl and/or alkenyl group containing 4 to 22 carbon atoms, G is a sugar unit containing 5 or 6 carbon atoms and p is a number of 1 to 10. They may be obtained by the relevant methods of preparative organic chemistry, for example by acid-catalyzed acetalization of glucose with fatty alcohols. The alkyl and/or alkenyl oligoglycosides may be derived from aldoses or ketoses containing 5 or 6 carbon atoms, preferably from glucose. Accordingly, the preferred alkyl and/or alkenyl oligoglycosides are alkyl and/or alkenyl oligoglucosides. The index p in general formula (III) indicates the degree of oligomerization (DP), i.e. the distribution of mono- and oligoglycosides, and is a number of 1 to 10. Whereas p in a given compound must always be an integer and, above all, may assume a value of 1 to 6, the value p for a certain alkyl oligoglycoside is an analytically determined calculated quantity which is mostly a broken number. Alkyl and/or alkenyl oligoglycosides with an average degree of oligomerization p of 1.1 to 3.0 are preferably used. Alkyl and/or alkenyl glycosides with a degree of oligomerization below 1.7 and, more particularly, between 1.2 and 1.4 are preferred from the applicational point of view. The alkyl or alkenyl group $R^5$ may be derived from primary alcohols containing 4 to 11 carbon atoms and preferably 8 to 10 carbon atoms. Typical examples are butanol, caproic alcohol, caprylic alcohol, capric alcohol and undecyl alcohol and the technical mixtures thereof obtained, for example, in the hydrogenation of technical fatty acid methyl esters or in the hydrogenation of aldehydes from Roelen's oxosynthesis. Alkyl oligoglucosides with a chain length of $C_8$ to $C_{10}$ (DP=1 to 3), which are obtained as first runnings in the separation of technical $C_{8-18}$ cocofatty alcohol by distillation and which contain less than 6% by weight of $C_{12}$ alcohol as an impurity, and alkyl oligoglucosides based on technical $C_{9/11}$ alcohols (DP=1 to 3), are preferably used. In addition, the alkyl or alkenyl group $R^5$ may be derived from primary alcohols containing 12 to 22 carbon atoms, preferably 12 to 14 carbon atoms. Typical examples are lauryl alcohol, myristyl alcohol, cetyl alcohol, palmitoleyl alcohol, stearyl alcohol, isostearyl alcohol, oleyl alcohol, elaidyl alcohol, petroselinyl alcohol, arachyl alcohol, gadoleyl alcohol, behenyl alcohol, erucyl alcohol, brassidyl alcohol and the technical mixtures thereof obtained as described above. Alkyl oligoglucosides based on hydrogenated $C_{12/14}$ cocoalcohol with a DP of 1 to 3 are preferred.

Oils

The preparations may additionally contain oils such as, for example, Guerbet alcohols based on fatty alcohols containing 6 to 18 and preferably 8 to 10 carbon atoms, esters of linear $C_{6-22}$ fatty acids with linear $C_{6-22}$ fatty alcohols, esters of branched $C_{6-13}$ carboxylic acids with linear $C_{6-22}$ fatty alcohols, esters of linear $C_{6-22}$ fatty acids with branched alcohols, more particularly 2-ethyl hexanol, esters of linear and/or branched fatty acids with polyhydric alcohols (for example propylene glycol, dimer diol or trimer triol) and/or Guerbet alcohols, triglycerides based on $C_{6-10}$ fatty acids, esters of $C_{6-22}$ fatty alcohols and/or Guerbet alcohols with aromatic carboxylic acids, more particularly benzoic acid, vegetable oils, branched primary alcohols, substituted cyclohexanes, linear $C_{6-22}$ fatty alcohol carbonates, Guerbet carbonates, dialkyl ethers, silicone oils and/or aliphatic or naphthenic hydrocarbons.

Preparations

Typical refatting preparations which are intended to illustrate the present invention may have a composition of the type shown by way of example in Table 1 below:

TABLE 1

Refatting compositions (preferred ranges in brackets); water to 100% by weight

| Component | Example | Percentage (by weight) |
|---|---|---|
| Fatty acid partial glyceride | Glyceryl laurate | 20 to 40 (30 to 35) |
| Monoglyceride suifate | Sodium cocomonoglycerol sulfate | 5 to 25 (10 to 20) |
| Alkyl oligoglucoside | Decyl polyglucose | 10 to 60 (20 to 50) |
| Oil | Dicaprylyl ether | 0 to 20 (1 to 10) |
| Glycerine | | 0 to 30 (1 to 25) |

If necessary, the preparations according to the invention may contain quantities of 0.5 to 25% by weight and preferably 1 to 15% by weight of glycerine and/or water.

Production in situ

The preparations according to the invention may readily be produced by mixing components (a) and (b). In one particularly advantageous embodiment, however, the present invention also relates to a process for the production of cosmetic preparations with refatting properties in which fatty acid partial glycerides are contacted with a less than stoichiometric quantity of a sulfating agent and the resulting acidic sulfation products are subsequently neutralized with aqueous bases. In practice, this means that the fatty acid partial glycerides are only partly sulfated and that the mixing ratio is adjusted through the degree of sulfation and hence through the quantity of sulfating agent used.

Sulfation and Neutralization

The reaction of the partial glycerides with suitable sulfating agents, preferably gaseous sulfur trioxide or chlorosulfonic acid, may be carried out in the same way as described for fatty acid lower alkyl esters in J. Falbe (ed.), "Surfactants in Consumer Products"; Springer Verlag, Berlin-Heidelberg, 1987, page 61, reactors operating on the falling-film principle being preferred. In this known process, the sulfur trioxide is diluted with an inert gas, preferably air or nitrogen, and used in the form of a gas mixture which contains the sulfating agent in a concentration of 1 to 8% by volume and, more particularly, 2 to 5% by volume. The molar ratio of partial glyceride to sulfating agent—based on the hydroxyl value of the starting materials—is 1:0.3 to 1:0.9, preferably from 1:0.5 to 1:0.85 and more preferably from 1:0.7 to 1:0.8. The sulfation reaction is carried out at temperatures of 35 to 90° C. and preferably at temperatures of 35 to 80° C. The acidic sulfation products accumulating during the sulfation reaction are stirred into aqueous bases, neutralized and adjusted to a pH value of 6.5 to 8.5. The neutralization step is carried out with bases selected from the group consisting of alkali metal hydroxides, such as sodium, potassium and lithium hydroxide, alkaline earth metal oxides and hydroxides, such as magnesium oxide, magnesium hydroxide, calcium oxide and calcium hydroxide, ammonia, mono, di- and tri-$C_{2-4}$-alkanolamines, for example mono-, di- and triethanolamine, and primary, secondary or tertiary $C_{1-4}$ alkyl amines. The neutralization bases are preferably used in the form of 5 to 55% by weight aqueous solutions, 25 to 50% by weight aqueous sodium hydroxide solution being preferred. After neutralization, the sulfation products may be bleached in known manner by addition of hydrogen peroxide or sodium hypochlorite solution to achieve a further lightening in color desirable for many applications. 0.2 to 2% by weight of hydrogen peroxide—expressed as 100% by weight substance—or corresponding quantities of sodium hypochlorite, based on the solids content in the solution of the sulfation products, are used for this purpose. The pH value of the solutions may be kept constant using suitable buffers, for example sodium phosphate or citric acid. In addition, preservation, for example with formaldehyde solution, p-hydroxybenzoate, sorbic acid or other known preservatives, is advisable for stabilization against bacterial infestation.

Commercial Applications

The preparations according to the invention are distinguished by high dermatological compatibility and excellent refatting properties. They are liquid and pumpable and can therefore be cold-pprocessed. They are free from nitrogen and, optionally, even from ethylene oxide and are sufficiently stabilized against microbial infestation, even in the absence of preservatives. They have thickening properties and are completely biodegradable. Accordingly, the present invention also relates to their use as refatting agents for the production of cosmetic preparations, for example for hair and body care.

The hair and body care formulations mentioned, for example hair shampoos, shower baths, foam baths, day creams, night creams, skin-care creams, nourishing creams, body lotions, emollients and the like may contain mild surfactants, emulsifiers, superfatting agents, stabilizers, waxes, consistency providers, thickeners, cationic polymers, silicone compounds, biogenic agents, antidandruff agents, film formers, preservatives, hydrotropes, solubilizers, UV filters, insect repellents, self-tanning agents, dyes and fragrances as further auxiliaries and additives.

Typical examples of suitable mild, i.e. dermatologically compatible, surfactants, are fatty alcohol polyglycol ether sulfates, mono- and/or dialkylsulfosuccinates, fatty acid isethionates, fatty acid sarcosinates, fatty acid taurides, fatty acid glutamates, ether carboxylic acids, fatty acid glucamides, alkyl amidobetaines and/or protein fatty acid condensates (preferably based on wheat proteins).

Suitable emulsifiers are, for example, nonionic surfactants from at least one of the following groups:

(1) adducts of 2 to 30 moles of ethylene oxide and/or 0 to 5 moles of propylene oxide with linear fatty alcohols containing 8 to 22 carbon atoms, with fatty acids containing 12 to 22 carbon atoms and with alkylphenols containing 8 to 15 carbon atoms in the alkyl group;

(2) glycerol monoesters and diesters and sorbitan monoesters and diesters of saturated and unsaturated fatty acids containing 6 to 22 carbon atoms and ethylene oxide adducts thereof;

(3) adducts of 15 to 60 moles of ethylene oxide with castor oil and/or hydrogenated castor oil;

(4) polyol esters and, in particular, polyglycerol esters such as, for example, polyglycerol polyricinoleate or polyglycerol poly-12-hydroxystearate. Mixtures of compounds from several of these classes are also suitable;

(5) adducts of 2 to 15 moles of ethylene oxide with castor oil and/or hydrogenated castor oil;

(6) partial esters based on linear, branched, unsaturated or saturated $C_{6/22}$ fatty acids, ricinoleic acid and 12-hydroxystearic acid and glycerol, polyglycerol, pentaerythritol, dipentaerythritol, sugar alcohols (for example sorbitol), alkyl glucosides (for example methyl glucoside, butyl glucoside, lauryl glucoside) and polyglucosides (for example cellulose);

(7) trialkyl phosphates and mono-, di- and/or tri-PEG-alkyl phosphates;

(8) wool wax alcohols;

(9) polysiloxane/polyalkyl polyether copolymers and corresponding derivatives;

(10) mixed esters of pentaerythritol, fatty acids, citric acid and fatty alcohol according to DE-PS 11 65 574 and/or mixed esters of fatty acids containing 6 to 22 carbon atoms, methyl glucose and polyols, preferably glycerol,

(11) polyalkylene glycols and

(12) hydrophobicized polyacrylates.

The addition products of ethylene oxide and/or propylene oxide with fatty alcohols, fatty acids, alkylphenols, glycerol monoesters and diesters and sorbitan monoesters and diesters of fatty acids or with castor oil are known commercially available products. They are homolog mixtures of which the average degree of alkoxylation corresponds to the ratio between the quantities of ethylene oxide and/or propylene oxide and substrate with which the addition reaction is carried out.

In addition, zwitterionic surfactants may be used as emulsifiers. Zwitterionic surfactants are surface-active compounds which contain at least one quaternary ammonium group and at least one carboxylate and one sulfonate group in the molecule. Particularly suitable zwitterionic surfactants are the so-called betaines, such as the N-alkyl-N,N-dimethyl ammonium glycinates, for example cocoalkyl dimethyl ammonium glycinate, N-acylaminopropyl-N,N-dimethyl ammonium glycinates, for example cocoacylaminopropyl dimethyl ammonium glycinate, and 2-alkyl-3-carboxymethyl-3-hydroxyethyl imidazolines containing 8 to 18 carbon atoms in the alkyl or acyl group and cocoacylaminoethyl hydroxyethyl carboxymethyl glycinate. The fatty acid amide derivative known under the CTFA name of Cocoamidopropyl Betaine is particularly preferred. Ampholytic surfactants are also suitable emulsifiers. Ampholytic surfactants are surface-active compounds which, in addition to a $C_{8/18}$ alkyl or acyl group, contain at least one free amino group and at least one —COOH— or —SO$_3$H— group in the molecule and which are capable of forming inner salts. Examples of suitable ampholytic surfactants are, N-alkyl glycines, N-alkyl propionic acids, N-alkylaminobutyric acids, N-alkyliminodipropionic acids, N-hydroxyethyl-N-alkylamidopropyl glycines, N-alkyl taurines, N-alkyl sarcosines, 2-alkylaminopropionic acids and alkylaminoacetic acids containing around 8 to 18 carbon atoms in the alkyl group. Particularly preferred ampholytic surfactants are N-cocoalkylaminopropionate, cocoacylaminoethyl aminopropionate and $C_{12/18}$ acyl sarcosine. Besides ampholytic emulsifiers, quaternary emulsifiers may also be used, those of the esterquat type, especially methylquaternized difatty acid triethanolamine ester salts, being particularly preferred.

Superfatting agents may be selected from such substances as, for example, lanolin and lecithin and also polyethoxylated or acylated lanolin and lecithin derivatives, polyol fatty acid esters and fatty acid alkanolamides, the fatty acid alkanolamides also serving as foam stabilizers. The consistency providers mainly used are fatty alcohols containing 12 to 22 and preferably 16 to 18 carbon atoms and partial glycerides. A combination of these substances with alkyl oligoglucosides and/or fatty acid N-methyl glucamides of the same chain length and/or polyglycerol poly-12-hydroxystearates is preferably used. Suitable thickeners are, for example, polysaccharides, more especially xanthan gum, guar-guar, agar-agar, alginates and tyloses, carboxymethyl cellulose and hydroxyethyl cellulose, also relatively high molecular weight polyethylene glycol monoesters and diesters of fatty acids, polyacrylates (for example Carbopols® [Goodrich] and Synthalens® [Sigma]), polyacrylamides, polyvinyl alcohol and polyvinyl pyrrolidone, surfactants such as, for example, ethoxylated fatty acid glycerides, esters of fatty acids with polyols, for example pentaerythritol or trimethylol propane, narrow-range fatty alcohol ethoxylates or alkyl oligoglucosides and electrolytes, such as sodium chloride and ammonium chloride.

Suitable cationic polymers are, for example, cationic cellulose derivatives such as, for example, the quaternized hydroxyethyl cellulose obtainable from Amerchol under the name of Polymer JR 400®), cationic starch, copolymers of diallyl ammonium salts and acrylamides, quaternized vinyl pyrrolidone/vinyl imidazole polymers such as, for example, Luviquat® (BASF), condensation products of polyglycols and amines, quaternized collagen polypeptides such as, for example, Lauryldimonium Hydroxypropyl Hydrolyzed Collagen (Lamequat® L, Grünau), quaternized wheat polypeptides, polyethyleneimine, cationic silicone polymers such as, for example, Amidomethicone, copolymers of adipic acid and dimethyl-aminohydroxypropyl diethylenetriamine (Cartaretine®, Sandoz), copolymers of acrylic acid with dimethyl diallyl ammonium chloride (Merquat® 550, Chemviron), polyaminopolyamides as described, for example, in FR-A 2 252 840 and crosslinked water-soluble polymers thereof, cationic chitin derivatives such as, for example, quaternized chitosan, optionally in microcrystalline distribution, condensation products of dihaloalkyls, for example dibromobutane, with bis-dialkylamines, for example bis-dimethylamino-1,3-propane, cationic guar gum such as, for example, Jaguar®CBS, Jaguar®C-17, Jaguar®C-16 of Celanese, quaternized ammonium salt polymers such as, for example, Mirapol® A-15, Mirapol® AD-1, Mirapol® AZ-1 of Miranol.

Suitable silicone compounds are are, for example, dimethyl polysiloxanes, methyl phenyl polysiloxanes, cyclic silicones and amino-, fatty acid-, alcohol-, polyether-, epoxy-, fluorine- and/or alkyl-modified silicones which may be present both in liquid form and in resin-like form at room temperature. Typical examples of fats are glycerides while suitable waxes are inter alia beeswax, carnauba wax, candelilla wax, montan wax, paraffin wax or microwaxes, optionally in combination with hydrophilic waxes, for example cetostearyl alcohol, or partial glycerides. The pearlescent waxes used may be, in particular, mono- and difatty acid esters of polyalkylene glycols, partial glycerides or esters of fatty alcohols with polybasic carboxylic acids or hydroxycarboxylic acids. Suitable stabilizers are metal salts of fatty acids such as, for example, magnesium, aluminium and/or zinc stearates. Biogenic agents in the context of the invention are, for example, tocopherol, tocopherol acetate, tocopherol palmitate, ascorbic acid, retinol, bisabolol, allantoin, phytantriol, panthenol, AHA acids, plant extracts and vitamin complexes. Suitable antidandruff agents are Climbazol, Octopirox and zinc pyrithione. Typical film formers are, for example, chitosan, microcrystalline chitosan, quaternized chitosan, polyvinyl pyrrolidone, vinyl pyrrolidone/vinyl acetate copolymers, polymers of the acrylic acid series, quaternary cellulose derivatives, collagen, hyaluronic acid and salts thereof and similar compounds.

In the context of the invention, UV filters are organic compounds which are capable of absorbing ultraviolet rays and of releasing the energy absorbed in the form of longer wave radiation, for example heat. Typical examples are 4-aminobenzoic acid and esters and derivatives thereof (for example 2-ethylhexyl-p-dimethylaminobenzoate or p-dimethylaminobenzoic acid octyl ester), methoxycinnamic acid and derivatives thereof (for example 4-methoxycinnamic acid-2-ethylhexyl ester), benzophenones (for example oxybenzone, 2-hydroxy4-methoxybenzophenone), dibenzoyl methanes, salicylate esters, 2-phenyl benzimidazole-5-sulfonic acid, 1-(4-tert.butylphenyl3-(4'-methoxyphenyl)-propane-1,3dione, 3(4'-methyl) benzylidenebornan-2-one, methyl-benzylidene camphor and the like. Other suitable UV filters are finely disperse metal oxides and salts, for example titanium dioxide, zinc oxide, iron oxide, aluminium oxide, cerium oxide, zirconium oxide, silicates (talcum) and barium sulfate. The particles should have an average diameter of less than 100 nm, preferably from 5 to 50 nm and more preferably from 15 to 30 nm. They may be spherical in shape although ellipsoidal particles or other non-spherical particles may also be used. Besides the two above-mentioned groups of primary light filters, secondary light filters of the antioxidant type, which interrupt the photochemical reaction chain initiated when UV radiation penetrates into the skin, may also be used. Typical examples of these secondary light filters are Superoxid-Dismutase, tocopherols (vitamin E) and ascorbic acid (vitamin C).

In addition, hydrotropes, such as, for example, ethanol, isopropyl alcohol or polyols may be used to improve flow behavior. Suitable polyols preferably contain 2 to 15 carbon atoms and at least two hydroxyl groups. Typical examples are glycerol;

alkylene glycols such as, for example, ethylene glycol, diethylene glycol, propylene glycol, butylene glycol, hexylene glycol and polyethylene glycols having an average molecular weight of 100 to 1,000 dalton;

technical oligoglycerol mixtures with a degree of self-condensation of 1.5 to 10 such as, for example, technical diglycerol mixtures with a diglycerol content of 40 to 50% by weight;

methylol compounds such as, in particular, trimethylol ethane, trimethylol propane, trimethylol butane, pentaerythritol and dipentaerythritol;

lower alkyl glucosides, particularly those containing 1 to 8 carbon atoms in the alkyl group, for example methyl and butyl glucoside;

sugar alcohols containing 5 to 12 carbon atoms such as, for example, sorbitol or mannitol;

sugars containing 5 to 12 carbon atoms such as, for example, glucose or sucrose and aminosugars such as, for example, glucamine.

Suitable preservatives are, for example, phenoxyethanol, formaldehyde solution, parabens, pentanediol or sorbic acid. Suitable insect repellents are N,N-diethyl-m-toluamide, pentane-1,2-diol or Insect Repellent 3535. A suitable self-tanning agent is dihydroxyacetone. Suitable dyes are any of the substances suitable and approved for cosmetic purposes as listed, for example, in the publication "Kosmetische Färbemittel" of the Farbstoffkommission der Deutschen Forschungsgemeinschaft, Verlag Chemie, Weinheim, 1984, pages 81 to 106, These dyes are normally used in concentrations of 0.001 to 0.1% by weight, based on the mixture as a whole.

The total percentage content of auxiliaries and additives may be from 1 to 50% by weight and is preferably from 5 to 40% by weight, based on the particular formulation. The formulations may be prepared by standard cold or hot processes and are preferably produced by the phase inversion temperature method.

EXAMPLES

Sulfation of Lauric Acid Monoglyceride

In a continuous falling-film reactor (length 120 cm, cross-section 1 cm, educt throughput 600 g/h) with a cooling jacket and a lateral inlet for $SO_3$ gas, 1650 g (5 moles) of technical lauric acid monoglyceride (Monomols 90 L-12) were reacted with sulfur trioxide at 95° C. The $SO_3$ was used in a ratio of 0.5 mole to 1 mole of hydroxyl groups present in the partial ester. The sulfur trioxide had been driven out by heating from a corresponding quantity of 65% by weight oleum, diluted with nitrogen to a concentration of 5% by volume and contacted through a nozzle with the monoglyceride film. It was then stirred together with 37% by weight sodium hydroxide solution into a 1% by weight solution of sodium triphosphate and neutralized at pH 6.5 to 8. The reaction product contained 10.9% by weight of lauric acid monoglyceride sulfate sodium salt, 7.3% by weight of lauric acid monoglyceride, 0.4% by weight of sodium laurate, 1.5% by weight of sodium sulfate and water to 100% by weight.

Transepidermal Water Loss

To evaluate dermatological compatibility, the transepidermal water loss was investigated using pig epidermis. To this end, defined pieces of skin were treated with the various test solutions for 30 minutes at 40° C. and the TEWL value was gravimetrically determined. The results are set out in Table 2. The TEWL value is the ratio in percent of the transepidermal water loss of an untreated sample to that of a treated sample. The lower value, the better the dermatological compatibility. Formulations 1 to 4 correspond to the invention while mixtures C1 and C2 are intended for comparison.

TABLE 1

Transepidermal water loss (TWEL)

| Composition/Performance | 1 | 2 | 3 | 4 | C1 | C2 |
|---|---|---|---|---|---|---|
| Sodium Cocomonogh/Cerdi Sulfate | 15.0 | 15.0 | 15.0 | 15.0 | — | — |
| Sodium Laureth Sulfate | — | — | — | — | 15.0 | 15.0 |
| Coco Glucosides | — | — | 1.0 | 1.0 | — | 1.0 |
| Cocoamidopropyl Betaine | — | — | — | 1.0 | — | — |
| Glyceryl Laurate | 3.5 | — | — | — | — | — |
| Glyceryl Stearate | — | 3.5 | 2.5 | 1.5 | 3.5 | 2.5 |
| Water | | | to 100 | | | |
| TEWL [% rel.] | 2.1 | 2.2 | 1.9 | 1.7 | 3.3 | 3.1 |

The Examples and Comparison Examples clearly show that the preparations according to the invention produce a far lower transepidermal water loss than the comparison mixtures and, accordingly, have significantly better dermatological compatibility. Model formulations for a hair rinse (5), various shower baths (6 to 8) and a shampoo formulation (9) are shown in Table 3 below.

TABLE 3

Model formulations (quantities in % by weight)

| Composition | 5 | 6 | 7 | 8 | 9 |
|---|---|---|---|---|---|
| Sodium Cocomonoglycerol Sulfate | 1.0 | 38.0 | 2.0 | 20.0 | 25.0 |
| Sodium Laureth Sulfate (and) Lauryl Polyglucose | — | — | — | 20.0 | — |
| Lauryl Polyglucose | 2.0 | — | — | — | — |
| Decyl Polyglucose | — | 7.0 | 5.0 | — | 5.0 |
| Hexyl Polyglucose (and) Hexyl Alcohol | 3.0 | — | — | — | — |
| Cocamidopropyl Betaine | — | — | 20.0 | — | 8.0 |
| Ceteareth-20 | — | — | — | 1.0 | — |
| Hydrolyzed keratin | 2.3 | — | — | — | — |
| Hydrolyzed Collagen | — | — | 1.0 | — | — |
| Lauryldimmonium hydroxypropyl hydrolyzed collagen | 1.0 | 3.0 | 1.0 | 1.0 | 3.0 |
| Octyldodecanol | — | — | — | 3.0 | — |
| Polyglyceryl-3 Diisostearate | 1.0 | — | — | — | — |
| PEG-2-Ceteareth-9 | — | — | — | — | 1.0 |
| Decyl Oleate | 1.0 | — | — | — | — |
| Glyceryl Stearate | — | — | — | 4.0 | — |
| Glyceryl Isostearate | — | 3.0 | 1.0 | — | 2.0 |
| Glyceryl Oleate | 0.5 | 0.5 | — | — | — |
| Glycol Distearate (and) Cocamidopropyl Betaine | — | — | 5.0 | — | — |
| Laureth-2 | — | 1.0 | 0.5 | — | 1.5 |
| Sodium Styrenel Acrylate Copolymer | — | — | 2.0 | 1.0 | — |
| Water | | | to 100 | | |

What is claimed is:

1. A composition having refatting properties comprising:
   (a) at least one monoglyceride (ether) sulfate; and
   (b) at least one fatty acid partial glyceride;
   wherein the weight ratio of component (a) to component (b) is from about 30:70 to about 99:1.

2. The composition of claim 1 wherein the at least one monoglyceride (ether) sulfate has the formula

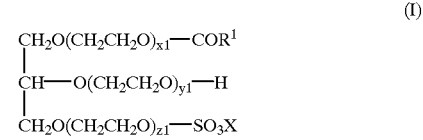

(I)

in which $R^1CO$ is a linear or branched acyl group containing from 6 to 22 carbon atoms, x1, y1 and z1 taken together stand for 0 or for a number of from 1 to 30 and x is an alkali metal or alkaline earth metal.

3. The composition of claim 1 wherein the at least one fatty acid partial glyceride has the formula

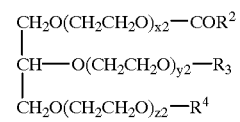

where $R^2CO$ is a linear or branched acyl group containing from 6 to 22 carbon atoms, x2, y2 and z2 taken together stand for 0 or for a number of from 1 to 30, $R^3$ and $R^4$ independently of one another have the same meaning as $R^2CO$ or represent hydrogen, with the proviso that $R^3$ and $R^4$ cannot both be an acyl group.

4. The composition of claim 2 wherein the at least one fatty acid partial glyceride has the formula $$\begin{array}{c} CH_2O(CH_2CH_2O)_{x2}-COR^2 \\ | \\ CH-O(CH_2CH_2O)_{y2}-R^3 \\ | \\ CH_2O(CH_2CH_2O)_{z2}-R^4 \end{array} \quad (II)$$

where $R^2CO$ is a linear or branched acyl group containing from 6 to 22 carbon atoms, x2, y2 and z2 taken together stand for 0 or for a number of from 1 to 30, $R^3$ and $R^4$ independently of one another have the same meaning as $R^2CO$ or represent hydrogen, with the proviso that $R^3$ and $R^4$ cannot both be an acyl group.

5. The composition of claim 4 wherein the weight ratio of component (a) to component (b) is from about 30:70 to about 99:1.

6. The composition of claim 3 wherein x2, y2 and z2 taken together stand for a number of from 2 to 10.

7. The composition of claim 4 wherein x2, y2 and z2 taken together stand for a number of from 2 to 10.

8. The composition of claim 4 wherein x1, y1, and z1 taken together stand for a a number of from 2 to 10.

9. The composition of claim 1 wherein said weight ratio is from about 50:50 to about 90:10.

10. The composition of claim 5 wherein said weight ratio is from about 50:50 to about 90:10.

11. The composition of claim 1 wherein said weight ratio is from about 70:30 to about 80:20.

12. The composition of claim 5 wherein said weight ratio is from about 70:30 to about 80:20.

13. The composition of claim 1 wherein the composition also contains at least one of an alkyl or alkenyl polyglycoside of the formula:

$$R^5O-(G)_p \quad (III)$$

in which $R^5$ is an alkyl and/or alkenyl group containing 4 to 22 carbon atoms, G is a sugar unit containing 5 or 6 carbon atoms and p is a number of 1 to 10.

14. The composition of claim 4 wherein in formula I the $-COR^1$ group is a linear acyl group containing from 8 to 18 carbon atoms.

15. The composition of claim 14 wherein in formula II the $R^2OC-$ group contains from 12 to 18 carbon atoms.

16. The composition of claim 1 wherein the composition comprises a mixture of cocomonoglyceride sulfites and cocofatty acid monoglycerides.

17. The composition of claim 1 wherein the composition also contains at least one oil selected from the group consisting of Guerbet alcohols containing 6 to 18 carbon atoms, esters of linear $C_{6-22}$ fatty acids with linear $C_{6-22}$ fatty alcohols, esters of branched $C_{6-13}$ carboxylic acids with linear $C_{6-22}$ fatty alcohols, esters of linear $C_{6-22}$ fatty acids with branched alcohols, esters of linear or branched fatty acids with polyhydric alcohols or Guerbet alcohols, triglycerides based on $C_{6-10}$ fatty acids, esters of $C_{6-22}$ fatty alcohols or Guerbet alcohols with aromatic carboxylic acids, vegetable oils, branched primary alcohols, substituted cyclohexanes, linear $C_{6-22}$ fatty alcohol carbonates, Guerbet carbonates, dialkyl ethers, silicone oils, and aliphatic or naphthenic hydrocarbons.

18. In a cosmetic preparation, the improvement wherein the preparation contains the refitting composition of claim 1.

19. In a cosmetic preparation, the improvement wherein the preparation contains the refitting composition of claim 4.

20. The composition of claim 1 wherein the ratio by weight of a): b) is from 30:70 to 99:1.

21. The composition of claim 20 wherein said ratio is from 50:50 to 90:10.

22. The composition of claim 20 wherein said ratio is from 70:30 to 80:20.

* * * * *